United States Patent
Stanley et al.

(10) Patent No.: US 11,224,646 B2
(45) Date of Patent: Jan. 18, 2022

(54) INTRANASAL DELIVERY OF A CYCLIC-DI-NUCLEOTIDE ADJUVANTED VACCINE FOR TUBERCULOSIS

(71) Applicant: The Regents of the University of California, Oakland, CA (US)

(72) Inventors: Sarah Stanley, Berkeley, CA (US); Erik Van Dis, Berkeley, CA (US); Kimberly Sogi, Berkeley, CA (US); Daniel A. Portnoy, Berkeley, CA (US); Chris Rae, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 23 days.

(21) Appl. No.: 16/921,959

(22) Filed: Jul. 7, 2020

(65) Prior Publication Data
US 2020/0338182 A1    Oct. 29, 2020

Related U.S. Application Data

(63) Continuation of application No. PCT/US2019/014380, filed on Jan. 19, 2019.

(60) Provisional application No. 62/622,718, filed on Jan. 26, 2018.

(51) Int. Cl.
*A61K 39/04* (2006.01)
*A61P 31/06* (2006.01)
*A61K 39/00* (2006.01)

(52) U.S. Cl.
CPC .............. *A61K 39/04* (2013.01); *A61P 31/06* (2018.01); *A61K 2039/5256* (2013.01); *A61K 2039/53* (2013.01); *A61K 2039/543* (2013.01); *A61K 2039/545* (2013.01); *A61K 2039/55505* (2013.01); *A61K 2039/55511* (2013.01); *A61K 2039/55561* (2013.01); *A61K 2039/55566* (2013.01)

(58) Field of Classification Search
CPC ........ A61K 2039/555505; A61K 39/04; A61K 2300/00; A61K 31/7084; A61K 39/02; A61P 31/06; A61P 31/04; A61P 37/04; A61P 11/02; C07H 19/23; C07D 519/00
See application file for complete search history.

(56) References Cited

U.S. PATENT DOCUMENTS 8,871,436 B2 * 10/2014 Lopez ..................... A61P 37/00
435/5

* cited by examiner

*Primary Examiner* — Bao Q Li
(74) *Attorney, Agent, or Firm* — Richard Aron Osman

(57) ABSTRACT

A vaccine against *Mycobacterium tuberculosis* (*M. tuberculosis*) formulated for intranasal administration, comprises a first vaccine component comprising one or more *M. tuberculosis*, *Mycobacterium vaccae* (*M. vaccae*) or *Mycobacteroium bovis* (*M. bovis*) antigens, and a second vaccine component comprising a Stimulator of Interferon Genes (STING) activator.

18 Claims, No Drawings

INTRANASAL DELIVERY OF A CYCLIC-DI-NUCLEOTIDE ADJUVANTED VACCINE FOR TUBERCULOSIS

This invention was made with government support under Grant Number AI091976 awarded by the National Institutes of Health. The government has certain rights in the invention.

INTRODUCTION

Infection with *Mycobacterium tuberculosis* continues to be a leading cause of death worldwide, in part due to the lack of an effective vaccine (Young & Dye 2006). The current vaccine for *M. tuberculosis*, Bacille Calmette-Guérin (BCG), is widely administered (Floyd 2016), yet its protective efficacy against adult pulmonary tuberculosis (TB) is variable, ranging from 0-80% in clinical trials (Andersen & Doherty 2005). Additionally, as a live attenuated vaccine, BCG is not recommended for individuals with a compromised immune system, including infants with HIV (Marais et al. 2016). Significant effort has focused on developing vaccines that can either replace or boost BCG to generate a protective immune response against pulmonary TB. Currently, there are 12 vaccine candidates for TB in clinical trials, 8 of which are novel protein subunit vaccines (Kaufmann et al. 2017). One benefit of subunit vaccines is that they generally exhibit better safety profiles than live attenuated vaccines that cannot always be given to immunocompromised individuals. However, subunit vaccines require an adjuvant to elicit a strong memory immune response to the vaccine antigen, and there is a lack of clinically approved adjuvants that elicit antigen-specific effector and long-lived memory CD4+ and CD8+ T cells (Iwasaki & Medzhitov 2010).

Cyclic dinucleotides (CDNs) were initially characterized as ubiquitous second messengers in bacteria (Tamayo et al. 2007) and were found to be pathogen-associated molecular patterns (PAMPs) recognized by the cytosolic surveillance pathway (McWhirter et al. 2009; Burdette et al. 2012). CDNs activate the cytosolic receptor Stimulator of Interferon Genes (STING), leading to signaling through multiple immune pathways: TBK1/IRF3 leading to type I IFN, classical inflammation via NF-κB, and STAT6-dependent gene expression (Burdette & Vance 2012; Burdette et al. 2012; McWhirter et al. 2009; Chen et al. 2011). A synthetic, human STING-activating CDN (ADU-S100) is currently in Phase I clinical trials as a cancer therapeutic alone and in combination with checkpoint inhibition (Clinical trials.gov #NCT02675439 and #NCT03172936), and various other CDN molecules are also known (Corrales et al. 2015; Corrales et al. 2016).

Treatment with CDNs stimulates innate immune cells to control *Klebsiella pneumoniae* and *Staphylococcus aureus* infection in vivo (Karaolis, Means, et al. 2007; Karaolis, Newstead, et al. 2007). Additionally, immunizing with model antigens in conjunction with CDNs results in distinct immune responses depending on the route of delivery, with subcutaneous administration leading to a Th1/Th2 response and mucosal administration leading to a Th17 response (Ebensen et al. 2011). CDNs have also been shown to elicit protective antibody-based immunity when used as a vaccine adjuvant against the extracellular bacterial pathogens *S. aureus* and *Streptococcus pneumoniae* (Ebensen, Schulze, Riese, Morr, et al. 2007; Ebensen, Schulze, Riese, Link, et al. 2007; Madhun et al. 2011; Libanova et al. 2010; Ogunniyi et al. 2008; Hu et al. 2009; Dubensky et al. 2013; Yan et al. 2009). Finally, CDNs are under investigation as promising agents for cancer immunotherapy (Woo et al. 2014; Chandra et al. 2014; Hanson et al. 2015). No study has demonstrated that a CDN adjuvant can elicit T cell-based protective immunity against an intracellular bacterial pathogen.

CDNs activate the same cytosolic surveillance pathways as *M. tuberculosis* and other intracellular pathogens (Watson et al. 2015; Wassermann et al. 2015; Dey et al. 2015). Other vaccine adjuvants under development for TB utilize toll-like receptor (TLR) agonists or TB cell wall lipids (Agger 2016) that are not known to activate STING or any other cytosolic surveillance pathway. In addition, BCG does not activate STING due to the loss of a key virulence mechanism (Watson et al. 2015). Furthermore, Th17 T cells are important for the protection conferred by BCG in mice (Khader et al. 2007).

SUMMARY OF THE INVENTION

The invention provides methods and compositions for vaccination of a human against *Mycobacterium tuberculosis* (*M. tuberculosis*).

In one aspect the invention provides a method of prophylactic or therapeutic vaccination of a human against *Mycobacterium tuberculosis* (*M. tuberculosis*) comprising:
  intranasally administering a first vaccine component comprising one or more *M. tuberculosis*, *Mycobacterium vaccae* (*M. vaccae*) or *Mycobacteroium bovis* (*M. bovis*) antigens,
  intranasally administering a second vaccine component comprising a Stimulator of Interferon Genes (STING) activator.

In another aspect the invention provides a prophylactic or therapeutic vaccine against *Mycobacterium tuberculosis* (*M. tuberculosis*) comprising:
  a first vaccine component comprising one or more *M. tuberculosis*, *Mycobacterium vaccae* (*M. vaccae*) or *Mycobacteroium bovis* (*M. bovis*) antigens,
  a second vaccine component comprising a Stimulator of Interferon Genes (STING) activator, and
  a pharmaceutical excipient for intranasal administration, e.g., an aqueous vehicle, such as
  a buffered saline solution.

In embodiments:
  the first vaccine component comprises *M. bovis* and/or *M. vaccae*;
  the first vaccine component comprises *Bacillus* Calmette-Guérin (BCG);
  the first vaccine component comprises one or more recombinantly expressed proteins that comprise one or more antigens from *M. tuberculosis, M. vaccae,* or *M. bovis*;
  the first vaccine component comprises one or more recombinantly expressed proteins that comprise one or more antigens from *M. tuberculosis*;
  the first vaccine component comprises a viral vector modified to express one or more proteins that comprise one or more antigens from *M. tuberculosis, M. vaccae*, or *M. bovis*;
  the first vaccine component comprises a vaccinia virus modified to express one or more proteins that comprise one or more antigens from *M. tuberculosis*;
  the first vaccine component comprises one or more antigens selected from the group consisting of Ag85A, Ag85B, ESAT6, RpfD, RpfB, CFP-10, MPT-64, PstS1, Apa, GroES, GroEL, DnaK, EspC, PhoY2, Mtb8;

4, Mtb10; 4, HspX, Rv1733c, Rv2626c, Rv1886, Rv2875, Rv3407, and Rv3478;

the first vaccine component comprises a plurality (at least 2, 4, 8 or 12) of antigens selected from the group consisting of Ag85A, Ag85B, ESAT6, RpfD, RpfB, CFP-10, MPT-64, Pst-S1, Apa, GroES, GroEL, DnaK, EspC, PhoY2, Mtb8; 4, Mtb10; 4, HspX, Rv1733c, Rv2626c, Rv1886, Rv2875, Rv3407, and Rv3478, particularly a fusion protein comprising the plurality, particularly a 2Ag fusion of Ag85B and ESAT-6, a 3Ag fusion of Ag85B, ESAT-6 and CFP-10, or a 5Ag fusion of Ag85B, ESAT-6, Rv1733c, Rv2626c, and Rv2389c (RpfD);

the STING activator is a cyclic dinucleotide (CDN);

the CDN is a CDG or a cGAMP;

the CDN is a phosphodiesterase-resistant synthetic form, such as a dithio-CDN, including RR-CDN with sulfur atoms in the R,R stereochemical configuration in place of non-bridging oxygen atoms, such as RR-CDG or ML-RR-cGAMP, or RS-CDN, SR-CDN, or SS-CDN with sulfur atoms in the R,S, the S,R, or the S,S stereochemical configuration in place of non-bridging oxygen atoms;

the CDN is RR-CDG or ML-RR-cGAMP, preferably ML-RR-cGAMP;

the first vaccine component and the second vaccine component are co-administered as separate compositions;

the first vaccine component and the second vaccine component are administered as a single composition;

the composition is administered in an aqueous vehicle;

the vaccine composition for intranasal administration comprises a third vaccine component that is an adjuvant;

the adjuvant is selected from the group consisting of incomplete Freund's adjuvant (IFA), dimethyl dioctadecyl ammoniumbromide (DDA), RIBI adjuvant, Quil-A saponin, MF59, MPL, IC31, LTK63, CAF01, CpG oligos, Poly I:C, DEAE-Dextran, and aluminum hydroxide;

the first vaccine component is administered as a priming vaccine and the second vaccine component is administered as a boost component in a prime-boost vaccination protocol; and/or the first vaccine component and the second vaccine component are administered as a priming vaccine in a prime-boost vaccination protocol.

the first vaccine component and the second vaccine component are administered as a boost component in a prime-boost vaccination protocol.

the first vaccine component and the second vaccine component are administered as a boost component in a prime-boost vaccination protocol, wherein BCG is administered as a priming vaccine.

In another aspect the invention provides a vaccine formulated for intranasal administration, comprising:

a first vaccine component comprising one or more *M. tuberculosis, Mycobacterium vaccae* (*M. vaccae*) or *Mycobacteroium bovis* (*M. bovis*) antigens, and a second vaccine component comprising a Stimulator of Interferon Genes (STING) activator, wherein the first vaccine component and the second vaccine component are combined in an aqueous vehicle.

In embodiments:

the first vaccine component comprises *M. bovis* and/or *M. vaccae*;

the first vaccine component comprises *Bacillus* Calmette-Guérin (BCG);

the first vaccine component comprises one or more recombinantly expressed proteins that comprise one or more antigens from *M. tuberculosis, M. vaccae*, or *M. bovis*;

the first vaccine component comprises one or more recombinantly expressed proteins that comprise one or more antigens from *M. tuberculosis*;

the first vaccine component comprises a viral vector modified to express one or more proteins that comprise one or more antigens from *M. tuberculosis, M. vaccae*, or *M. bovis*;

the first vaccine component comprises a vaccinia virus modified to express one or more proteins that comprise one or more antigens from *M. tuberculosis*;

the first vaccine component comprises one or more antigens selected from the group consisting of Ag85A, Ag85B, ESAT6, RpfD, RpfB, CFP-10, MPT-64, Pst-S1, Apa, GroES, GroEL, DnaK, EspC, PhoY2, Mtb8; 4, Mtb10; 4, HspX, Rv1733c, Rv2626c, Rv1886, Rv2875, Rv3407, and Rv3478;

the first vaccine component comprises a plurality (2, 4, 8 or 12) of antigens selected from the group consisting of Ag85A, Ag85B, ESAT6, RpfD, RpfB, CFP-10, MPT-64, Pst-S1, Apa, GroES, GroEL, DnaK, EspC, PhoY2, Mtb8.4, Mtb10.4, HspX, Rv1733c, Rv2626c, Rv1886, Rv2875, Rv3407, and Rv3478, particularly a fusion protein comprising the plurality, particularly a 2Ag fusion of Ag85B and ESAT-6, a 3Ag fusion of Ag85B, ESAT-6 and CFP-10, or a 5Ag fusion of Ag85B, ESAT-6, Rv1733c, Rv2626c, and RpfD;

the STING activator is a cyclic dinucleotide (CDN);

the CDN is a CDG or a cGAMP;

the CDN is a phosphodiesterase-resistant synthetic form, such as RR-CDN with sulfur atoms in the R,R stereochemical configuration in place of non-bridging oxygen atoms, such as RR-CDG or ML-RR-cGAMP;

the CDN is RR-CDG or ML-RR-cGAMP;

the composition is administered in an aqueous vehicle;

the vaccine composition for intranasal administration comprises a third vaccine component that is an adjuvant;

the adjuvant is selected from the group consisting of incomplete Freund's adjuvant (IFA), dimethyl dioctadecyl ammoniumbromide (DDA), RIBI adjuvant, Quil-A saponin, MF59, MPL, IC31, LTK63, CAF01, CpG oligos, DEAE-Dextran, and aluminum hydroxide;

the vaccine is administered as a boost component in a prime-boost vaccination protocol; and/or the vaccine is administered as a priming vaccine in a prime-boost vaccination protocol.

The invention encompasses all combination of the particular embodiments recited herein, as if each combination had been laboriously recited.

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Activators of the cytosolic receptor Stimulator of Interferon Genes (STING) are useful as described herein as adjuvants for vaccine formulations delivered as inhalants, in particular for intranasal delivery. The term "STING activator", also referred to as a "STING agonist", as used herein, refers to a compound capable of binding to STING and activating STING Activation of STING activity may include, for example, stimulation of inflammatory cytokines, including interferons, such as type 1 interferons, including IFN-α, IFN-β, type 3 interferons, e.g., IFNγ, or various other proinflammatory cytokines and chemokines including but not limited to IP10, TNFα, IL-6, CXCL9, CXCL10, CCL4, CXCL11, CCL5, CCL3, or CCL8. STING agonist activity may also include stimulation of TANK binding kinase (TB K) 1 phosphorylation, STING phosphorylation, interferon regulatory factor (IRF) activation (e.g., IRF3 activation), NFκB activation, STAT6 activation, secretion of interferon-γ-inducible protein (IP-10), or other inflammatory proteins and cytokines. Suitable STING agonists may be determined, for example, by measuring the binding affinity of the compound to STING protein, and its activity may be determined, for example, by the ability of a compound to stimulate activation of the STING pathway using methods known in the art. For example, the binding affinity of the compound to STING can be determined using Differential Scanning Fluorometry (DSF) or Isothermal Titration Calorimetry (ITC) binding assays. Assays for the activity of the compounds as STING agonists include, for example, an interferon stimulation assay, a reporter gene assay (e.g., a hSTING wt assay, or a THP-1 Dual assay), a TBK1 activation assay, IP-10 assay, a STING Biochemical [3H]cGAMP Competition Assay, or other assays known to persons skilled in the art. STING Agonist activity may also be determined by the ability of a compound to increase the level of transcription of genes that encode proteins activated by STING or the STING pathway. Such activity may be detected, for example, using quantitative real time PCR, RNAseq, Nanostring or various assays for detection of secreted protein in mice or cells (cytokine bead array, ELISA). In some embodiments, an assay to test for activity of a compound in a STING knock-out cell line may be used to determine if the compound is specific for STING, wherein a compound that is specific for STING would not be expected to have activity in a cell line wherein the STING pathway is partially or wholly deleted. Exemplary STING agonist compounds, methods of synthesis, and assays for the identification of compounds as STING agonists, can be found, for example, in PCT publications WO 2014/189805; WO 2014/093936; WO2016/145102; WO 2017/075477; WO 2018009466; WO 2014/179335; WO 2005/030186; WO 2007/054279; WO 2011/003025; WO 2015/074145; WO 2015/185565; WO 2016/120305; WO 2017/093933; WO 2016/096174; WO 2016/096577; WO 2017/027645; WO 2017/027646; WO 2017/123657; WO 2017/123669; WO 2018/009648; WO 2018/009652; WO 2007/070598; WO 2017/004499; WO 2017/011622; WO 2018/013908; and WO 2017/011920. Preferred STING agonists include, without limit, cyclic dinucleotides such as those described in PCT publications WO 2014/189805; WO2016/145102; WO 2017/075477; WO 2018009466; WO 2005/030186; WO 2007/054279; WO 2011/003025; WO 2015/074145; WO 2015/185565; WO 2016/120305; WO 2017/093933; WO 2016/096174;

WO 2016/096577; WO 2017/027645; WO 2017/027646; WO 2017/123657; WO 2017/123669; WO 2018/009648; and WO 2018/009652, including any pharmaceutically acceptable salt, pharmaceutically acceptable solvate or pharmaceutically acceptable hydrate thereof. In some embodiments, the cyclic dinucleotide comprises adenine (A) and/or guanine (G), such as a cyclic diA (CDA), cyclic diG (CDG), or cyclic GA (cGAMP), including 3'3' linked (e.g. 3'3'-(G)(A)), 2'2' linked (e.g. 2'2'-(G)(A)), or mixed link (ML, e.g. 2'3'-(G)(A) or 3'2'-(G)(A)), including any derivatives thereof, and any pharmaceutically acceptable salt, pharmaceutically acceptable solvate or pharmaceutically acceptable hydrate thereof. In some embodiments, the STING agonist is RR-CDG, also referred to as 3'3'-RR-(G)(G) or dithio-[$R_P$, $R_P$]-cyclic-[G(3',5')pG(3',5')p] or ML-RR-cGAMP, also referred to as 2'3'-RR-(G)(A), or dithio-[$R_P$, $R_P$]-cyclic-[G(2',5')pA(3',5')p], including any pharmaceutically acceptable salt, pharmaceutically acceptable solvate or pharmaceutically acceptable hydrate thereof. The structures of RR-CDG and ML-RR-cGAMP are as follows:

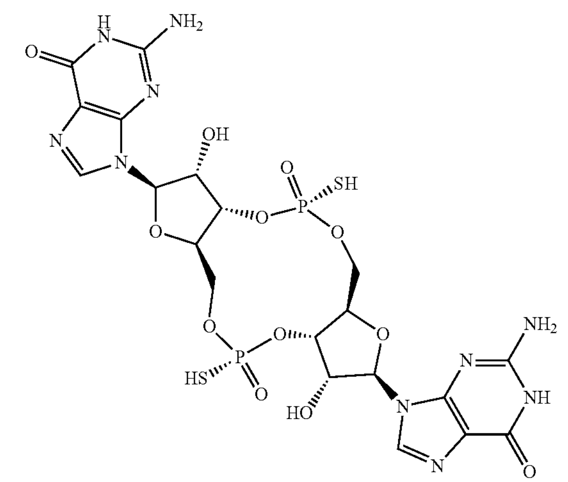

RR—CDG

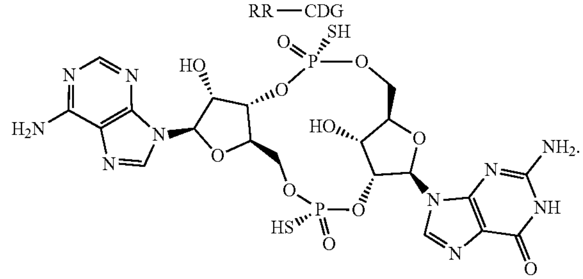

ML—RR—cGAMP

The vaccines as described herein, i.e. having at least a first vaccine component comprising one or more *M. tuberculosis, Mycobacterium vaccae* (*M. vaccae*) or *Mycobacteroium bovis* (*M. bovis*) antigens, and a second vaccine component comprising a STING activator, and optionally a third vaccine component that is an adjuvant, may be formulated for administration as an inhalant, preferable for intranasal delivery. Such formulations are readily known to one skilled in the art, and can be prepared by mixing the vaccine components, either separately or in the same formulation, with physiologically acceptable carriers, excipients, or stabilizers in the form of, e.g., lyophilized powders, slurries, aqueous solutions, or suspensions (see, e.g., Hardman et al., Goodman and Gilman's The Pharmacological Basis of Therapeutics, McGraw-Hill, New York, N.Y., 2001; Remington, The Science and Practice of Pharmacy 20 Edition, Mack Publishing Co., Easton, Pa.; and Nielloud and Marti-Mestres, Pharmaceutical Emulsions and Suspensions: $2^{nd}$ Edition, Marcel Dekker, Inc, New York). Thus in some embodiments the vaccine components as described herein are formulated as pharmaceutical compositions that may be delivered by intranasal sprays, inhalation, and/or other aerosol delivery vehicles. In some embodiments, the intranasal formulation is a sterile aqueous based formulation. The individual vaccine components may be formulated in the same formulation, or may be formulated separately to be co-administered, or administered by a certain dosing regimen, such as a prime-boost regimen. The vaccine components may be dissolved or suspended in solutions or mixtures of excipients, such as preservatives, viscosity modifiers, emulsifiers or buffering agents, and administered by delivering a spray containing a metered dose. In the formulation for intranasal delivery, the STING activator component, whether formulate with the remaining vaccine components, or separately, can be formulated to deliver a dose of 0.1-10000 µg, 0.1-5000 µg, 0.5-5000 µg, 0.5-2000 µg, 1-2000 µg, 1-1000 µg, 1-800 µg, 1-600 µg, 1-400 µg, 1-200 µg, 1-100 µg, or 1-50 µg.

The dose for delivery of the first vaccine component depends on the composition of the one or more antigens to be delivered. For example, the first vaccine component may be the BCG vaccine, which is an attenuated, live culture preparation of the *Bacillus* of Calmette and Guerin strain of *Mycobacterium bovis*, which can be administered e.g. percutaneously according to standard procedures, or intranasally, such as intranasally with a dose of $1\times10^3$ to $1\times10^{10}$, $1\times10^4$ to $1\times10^9$, $5\times10^4$ to $1\times10^9$, $5\times10^4$ to $1\times10^8$, or $1\times10^5$ to $1\times10^8$, colony forming units (CFU). The first component can be other attenuated, live culture preparations of *M. vaccae, M. tuberculosis*, or *M. bovis*, which can be dosed at similar levels (e.g., MTBVAC, used in clinical trials, is a human isolate of *M. tuberculosis* with stable deletion mutations in the phoP and fadD26 virulence genes). The one or more antigens of the first vaccine component can also be delivered in a viral vector modified to express the one or more proteins that comprise one or more antigens from *M. tuberculosis, M. vaccae*, or *M. bovis*. Suitable viral vectors include, but are not limited to, vaccinia virus (e.g. MVA), influenza virus, human parainfluenza virus, adenovirus (e.g. human Ad5, Ad26 and Ad35, and including simian derived adenovirus such as ChAd3 and ChAd63), pox virus, Vesicular stomatitis virus (VSV) and Cytomegalovirus (e.g. rCMV). In this case, the viral vector can be administered intranasally with a dose of $1\times10^4$ to $1\times10^{10}$, $5\times10^4$ to $1\times10^9$, $1\times10^5$ to $1\times10^9$, $1\times10^5$ to $5\times10^9$, or $1\times10^5$ to $1\times10^8$, plaque forming units (PFU) or infectious units (IFU). The first vaccine component may also be administered as a polypeptide, such as a fusion protein comprising the one or more antigens from *M. tuberculosis, M. vaccae*, or *M. bovis*, wherein the polypeptide can be administered intranasally with a dose of 0.1-10000 µg, 0.1-5000 µg, 0.5-5000 µg, 0.5-2000 µg, 1-2000 µg, 1-1000 µg, 1-800 µg, 1-600 µg, 1-400 µg, 1-200 µg, 1-100 µg, or 1-50 µg.

The one or more antigens from *M. tuberculosis, M. vaccae*, or *M. bovis*, can be one or more antigens known to those of skill in the art, or could be an antigen not yet recognized as suitable for eliciting an immune response to TB. The one or more antigens could be, for example, 1-20, 1-18, 1-16, 1-14, 1-12, 1-11, 1-10, 1-9, 1-8, 1-7, 1-6, 1-5, 1-4, 1-3, 1-2 or 1 antigen(s). Examples of antigens suitable for use in TB vaccines include, without limit, those described in Zvi et al. 2008 and Kassa et al. 2012. In some embodiments, the antigen comprises an antigenic portion of a protein expressed in *M. tuberculosis, M. vaccae*, or *M. bovis*, for example an antigenic polypeptide fragment of suitable length, including 8-5000, 8-4000, 8-3000, 8-2000, 8-1000, 8-900, 8-800, 8-700, 8-600, 8-500, 8-400, 8-300, 8-200, or 8-100 amino acids in length. In some embodiments, the antigen is an antigenic fragment of a protein expressed by a gene selected from the group consisting of rpf, ald, apa, acr, acg, gro, gro, devs, dna, esp, pho, fdx, hrp, hsp, esx, esx, esx, esx, icl, tuf, tgs, bfn, des, prp, PE, PPE, psp, pst, sak, irt, fbp, kat, mpt, an mbp, preferably selected from the group consisting of rpfA, rpfB, rpfC, rpfD, rpfE, ald, apa, acr, acg, groES, groEL, devs, dnaK, espC, phoY2, fdxA, hrp1, hspX, esxA, esxB, esxH, esxN, icl, tuf, tgs1, bfnB, desA1, prpD, PE11, PE35, PPE42, PPE55, PPE68, pspA, pstS1, sak5, irtB, fbpA, fbpB, katG, mpt63, and mbp64. In some embodiments, the one or more antigens are selected from the group consisting of MTB32A, MTB39A, Rv0079, Rv0081, Rv0140, Rv0288 (TB10.4), Rv0384c, Rv0440 (HSP65), Rv0467, Rv0574c, Rv0577, Rv0685, Rv0824c, Rv0867c, Rv1009, Rv1130, Rv1169c, Rv1174c (TB8.4), Rv1196, Rv1349, Rv1626, Rv1733c, Rv1734c, Rv1735c, Rv1737c, Rv1738, Rv1793, Rv1813c, Rv1884c, Rv1886c (Ag85B), Rv1908c, Rv1926c (MPT63), Rv1980c (MPT64), Rv1996, Rv1998, Rv2005c, Rv2006, Rv2007c, Rv2028c, Rv2029c, Rv2030c, Rv2031c (HSP16.3), Rv2032, Rv2389c, Rv2450c, Rv2608, Rv2620c, Rv2623, Rv2626c, Rv2627c, Rv2628, Rv2629, Rv2630, Rv2660, Rv2662, Rv2744c, Rv2780, Rv2875, Rv3044, Rv3127, Rv3130c, Rv3131, Rv3132c, Rv3223c, Rv3307, Rv3347c, Rv3407, Rv3478, Rv3619, Rv3620, Rv3804c (Ag85A), Rv3862c, Rv3873, Rv3874 (CFP-10), and Rv3875 (ESAT-6), or an antigenic fragment thereof. In some embodiments, the one or more antigens are selected from the group consisting of MTB32A, MTB39A, Rv0079, Rv0288 (TB10.4), Rv0867c, Rv1196, Rv1174c (TB8.4), Rv1733c, Rv1813c, Rv1886c (Ag85B), Rv1908c, Rv1980c (MPT64), Rv2029c, Rv2030c, Rv2031c (HSP16.3), Rv2032, Rv2389c, Rv2608, Rv2626c, Rv2627c, Rv2660, Rv2780, Rv2875, Rv3127, Rv3130c, Rv3132c, Rv3619, Rv3620, Rv3804c, Rv3873, Rv3874 (CFP-10), and Rv3875 (ESAT-6), or an antigenic fragment thereof. In some embodiments, the first vaccine component comprises a fusion protein comprising more than one antigen, wherein the fusion protein comprises at least one antigen selected from the group consisting of MTB32A, MTB39A, Rv0288, Rv1174c, Rv1733c, Rv1813c, Rv1886c, Rv1980c, Rv2389c, Rv2608, Rv2626c, Rv2660, Rv3619, Rv3620, Rv3804c, Rv3874, and Rv3875, or an antigenic fragment thereof.

The vaccination methods and compositions described herein optionally comprise a third vaccine component comprising an adjuvant. Vaccine adjuvants are well known to those of skill in the art, and are used to increase the ability of a vaccine to trigger, enhance, or prolong and immune response. Adjuvants include, without limit, cytokines, chemokines, bacterial nucleic acid sequences (such as CpG oligos), TLR agonists (such as TLR2, TLR4, TLR5, TLR7, TLR8, TLR9, lipoprotein, LPS, monophosphoryl lipid A, lipoteichoic acid, imiquimod, resiquimod, and the like), retinoic acid-inducible gene I (RIG-I) agonists (such as Poly I:C), lipids, liposomes, lipoproteins, lipopolypeptides, peptidoglycans (e.g. muramyl dipeptide), detoxified endotoxins, mineral oils, surface active substances such as lipolecithin, pluronic polyols, polyanions, peptides, oil or hydrocarbon emulsions, incomplete Freund's adjuvant (IFA), dimethyl dioctadecyl ammoniumbromide (DDA), RIBI adjuvant, Quil-A saponin, MF59, lipopolysaccharides (e.g. MPL), IC31, LTK63, CAF01, DEAE-Dextran, alum, aluminum hydroxide and aluminum phosphate.

The vaccination methods as described herein, wherein a first vaccine component and a second vaccine component are administered to a subject intranasally, include wherein the first and second vaccine components are administered together in the same formulation, or wherein the first and second vaccine components are co-administered in separate formulations. The co-administration of the first and second vaccine components means that the two components are administered at the same time, i.e. within 1 hour, within 30 minutes, within 10 minutes, within 5 minutes, or within 1 minute of each other. In some embodiments, the first and second vaccine components are administered in a prime-boost regimen, i.e. one of the components is administered days or weeks after the other component. In some embodiments, the first vaccine component is administered 1-28 days prior to the administration of the second component. In some embodiments, the first vaccine component is administered 1-28 days after the administration of the second component. In some embodiments vaccine comprising the first and second vaccine components, and optionally the third vaccine component is used as a prime or a boost in a prime-boost regimen. For example, a vaccine composition of the present invention comprises the first and second vaccine components, and optionally the third vaccine component formulated together for intranasal administration, and said vaccine composition is administered 1-28 days prior to or after another TB vaccine, such as the BCG vaccine, which can be administered by any suitable route, such as intradermal, subcutaneous or intranasal.

As described hereinafter, STING-activating adjuvants elicit antigen-specific Th1 and Th17 responses, recruitment of CXCR3+ KLRG1− parenchymal-homing T cells, and protection against *M. tuberculosis*. As discussed in the examples below, RR-CDG in combination with either the 2Ag fusion protein Ag85B-ESAT6 or the 5Ag fusion protein provided 1.5 logs of protection against aerosol challenge with virulent *M. tuberculosis* (Erdman strain) when used as a sole vaccine. In contrast to a similar 2Ag protein subunit vaccine formulated with the Th1 adjuvant dimethyldioctadecylammonium liposomes with monophosphoryl lipid A (DDA/MPL) (Carpenter et al. 2017) the protection afforded by CDN adjuvanted experimental 5Ag fusion protein vaccine was durable through 12 weeks post challenge.

This level of sustained efficacy is better than any vaccine adjuvant evaluated for use as a protein subunit vaccine for *M. tuberculosis* to date (Skeiky et al. 2004; Aagaard et al. 2011; Bertholet et al. 2010; Baldwin et al. 2012; Billeskov et al. 2012), and suggests that CDNs are capable of eliciting longer lived memory T cells than other vaccine adjuvants. Finally, the demonstration that a CDN adjuvanted vaccine can reduce TB disease in mice, presumably through T cell-dependent mechanisms, suggests that CDN adjuvants may be suitable for vaccination against other intracellular pathogens.

CDN activation of STING results in signaling via three distinct innate immune pathways (Burdette & Vance 2012), the best described being TBK1/IRF3 induction of type I IFNs (Ishikawa & Barber 2008). We found that the efficacy of CDNs as a vaccine adjuvant is dependent on STING but not on type I IFN in mice immunized SQ, and others have shown that the immune response to mucosally delivered CDG does not require type I IFN (Blaauboer et al. 2014). STING also activates NF-κB which induces classical pro-inflammatory cytokines including TNF-α, IL-1, IL-23 and IL-12 which may contribute to the efficacy of CDN adjuvants (Blaauboer et al. 2014). Furthermore, STING activates STAT-6-dependent expression of chemokines that are required for the antiviral responses of STING (Chen et al. 2011).

The 5Ag experimental vaccine fusion protein contains five *M. tuberculosis* proteins including Ag85B and ESAT-6, two well characterized immunodominant antigens (Weinrich Olsen et al. 2001; Horwitz et al. 1995; Baldwin et al. 1998; Brandt et al. 2000; Olsen et al. 2004; Langermans et al. 2005; Skjøt et al. 2000). In addition, 5Ag contains Rv1733c, Rv2626c, and RpfD, putative T cell antigens hypothesized to play a role in latency and/or reactivation from latency (Zvi et al. 2008). We observed significant T cell responses to ESAT-6 and Ag85B, and that a fusion protein of only ESAT-6 and Ag85B provided equivalent protective efficacy to that afforded by 5Ag; however Rv1733c, Rv2626c, and RpfD may also or alternatively be used with a CDN adjuvanted vaccine.

An ideal vaccine for *M. tuberculosis* would elicit memory T cells that traffic into the lung tissue, as these populations of T cells are protective when adoptively transferred to mice infected with *M. tuberculosis* (Sakai et al. 2014). We observed that vaccination with 5Ag/RR-CDG resulted in an increase in CD4+ CXCR3+ KLRG1− T cells, previously described to home to the lung parenchyma (Sakai et al. 2014), at 4 weeks post challenge. Despite inducing higher levels of parenchymal homing T cells, vaccination with 5Ag/RR-CDG resulted in a lower percentage of these cells producing IFN-γ compared to PBS immunized animals, indicating a novel T cell subset can mediate control in 5Ag/RR-CDG vaccinated mice.

STING-activating cyclic dinucleotides (CDNs) formulated in a protein subunit vaccine (5Ag/RR-CDG) elicit long-lasting protective immunity to *Mycobacterium tuberculosis*. Protection afforded by subcutaneous administration of this vaccine was equivalent to protection by the live attenuated vaccine strain Bacille Calmette-Guérin (BCG). This protective efficacy was STING-dependent but type I IFN-independent, and correlated with an increased frequency of a recently described subset of CXCR3-expressing T cells that localize to the lung parenchyma.

Furthermore, intranasal delivery of 5Ag/RR-CDG resulted in superior protection compared to BCG, significantly boosted BCG-based immunity, and elicited both Th1 and Th17 immune responses, the latter of which correlated with enhanced protection. Finally, ML-RR-cGAMP, a human STING agonist, has equivalent protective efficacy as RR-CDG in a protein subunit vaccine. Thus, a CDN adjuvanted protein subunit vaccine has the capability of eliciting a multi-faceted immune response that results in protection from infection by an intracellular pathogen.

The RR-CDG and ML-RR-cGAMP used in the following examples were provided by Aduro Biotech (synthesis as described in WO 2014/093936 and WO 2014/189805). Addavax (Invivogen, San Diego, Calif.) was used in the formulation of antigen and CDNs for vaccination. 5Ag fusion protein and peptide pools were provided by Aeras (Rockville, Md.). Mice used in the vaccination studies were CB6F1 or C57BL/6 (Jackson Laboratory, Bar Harbor, Me.), or Ifnar$^{-/-}$ mice or Sting$^{gt/gt}$ mice obtained from UC Berkeley (Vance lab and Raulet lab, respectively) and were bred in house. Sex and age matched controls were used for vaccine experiments.

Bacterial Culture—The *M. tuberculosis* strain Erdman was used for all challenges and *M. bovis* BCG (Pasteur) was used for all vaccinations. *M. tuberculosis* and BCG were grown in Middlebrook 7H9 liquid media supplemented with 10% albumin-dextrose-saline (*M. tuberculosis*) or 10% OADC (BCG), 0.4% glycerol, and 0.05% Tween 80 or on solid 7H10 agar plates supplemented with 10% Middlebrook OADC (BD Biosciences) and 0.4% glycerol. Frozen stocks of BCG were made from a single culture and used for all experiments.

Vaccinations—CDNs (5 µg) and 5Ag (3 µg) were formulated in 2% Addavax in PBS. Groups of 6 to 10 week old mice were vaccinated with RR-CDG three times at 4 week intervals with 100 µL at the base of the tail (50 µL on each flank) except BCG vaccinated mice. BCG vaccinated mice were injected once with 2.5-5e5 CFU/mouse in 100 µL of PBS SQ in the scruff of the neck. At the indicated week post-immunization, mice were bled (retro-orbital; 200 µL) for immunological assays (IFN-γ ELISPOT and/or ICS).

Challenge experiments with *M. tuberculosis*—Four weeks after the final vaccine injection, mice were infected by aerosol route with *M. tuberculosis* strain Erdman Aerosol infection was done using a Nebulizer and Full Body Inhalation Exposure System (Glas-Col, Terre Haute, Ind.). A total of 9 mL of culture was loaded into the nebulizer calibrated to deliver 100-200 bacteria per mouse as measured by CFU in lung one day following infection (data not shown). Unless stated otherwise, groups of five mice were sacrificed 4 and 12 weeks post-challenge to measure CFU and immune responses in the lungs (4 weeks only). For bacterial enumeration, one lung lobe (the largest) was homogenized in PBS plus 0.05% Tween 80, and serial dilutions were plated on 7H10 plates. CFUs were counted 21 days after plating. The remaining lung lobes were used for ICS.

Pre-challenge ELISPOT and ICS assays—Heparinized blood from five mice was analyzed separately or pooled and lymphocytes were isolated (Lympholyte-Mammal, Cedar Lane, cat #CL5115). For ELISPOTs, the lymphocytes (1e5 cells/well or 1e4 cells/well for Ag85B and ESAT6) were put in plates pre-coated with IFN-γ capture antibody (BD Biosciences #551881) containing splenocytes (1e5 cells/well) and peptide (2 µg/mL). Plates were incubated overnight, then washed and developed as per the BD Biosciences kit protocol. Spots were enumerated on a CTL Immunospot Analyzer. For ICS, cells were re-stimulated with no peptide, ESAT6 peptide (2 µg/mL), or Ag85B peptide (2 µg/mL), CFSE-labeled splenocyte feeder cells from an uninfected mouse (1e5 cells/well), GolgiPlug and GolgiStop for 5 hours at 37° C. Cells were kept at 4° C. overnight and then washed and stained with Live/Dead stain (Thermofisher, L34970), CD4 (BD, #564933), CD8 (BD, #563898), CD90.2 (BD, #561616), MHCII (Biolegend, #107606), Ly6G (BD, #551460), IFN-γ (eBioscience, #12-73111-81), TNF-α (BD, 506324), IL-17 (Biolegend, #506904). Data were collected using a BD LSR Fortessa flow cytometer with FACSDiva Software (BD) and analyzed using FlowJo Software (Tree Star Inc., Ashland, Oreg.).

Post-challenge Intracellular Cytokine Staining—Lungs (small lobes) were harvested 4 weeks post-challenge into cRPMI (RPMI-1640, 10% FBS, 1% Sodium pyruvate, 1% HEPES, 1% L-glutamine, 1% Non-essential amino acids, 1% pen/strep, 50 µM BME), dissociated and strained through a 40 µm strainer. Cells were re-stimulated with no peptide or Ag85B peptide (2 µg/mL), GolgiPlug and GolgiStop for 5 hours at 37° C. Cells were washed and stained with antibodies used for pre-challenge ICS and CXCR3 (Biolegend, #126522) and KLRG1 (Biolegend, #107606). Cells were fixed and permeabilized at RT for 20 mins and removed from the BSL3. Data were collected and analyzed as outlined above.

Example 1: A STING-Activating RR-CDG Adjuvanted Protein Subunit Vaccine Protects Against *M. tuberculosis* Infection The efficacy of CDNs as an adjuvant for *M. tuberculosis* antigens was tested with a synthetic form of CDG in which the non-bridging oxygen atoms were replaced with sulfur atoms in the R,R stereochemical configuration (RR-CDG) to prevent cleavage and inactivation by host cell phosphodiesterases (Corrales et al. 2015). RR-CDG was combined with the antigen 5Ag, a fusion of five *M. tuberculosis* proteins: Antigen-85B (Ag85B, Rv1886c), ESAT-6 (Rv3875), Rv1733c, Rv2626c, and RpfD (Rv2389c) (Zvi et al. 2008). Ag85B and ESAT-6 are established immunogenic TB antigens that have been tested in a variety of subunit vaccines and have been shown to elicit T cell responses in humans (Weinrich Olsen et al. 2001; Horwitz et al. 1995; Baldwin et al. 1998; Brandt et al. 2000; Olsen et al. 2004; Langermans et al. 2005). Rv1733, Rv2626c, and RpfD were identified in a bioinformatics analysis that identified potential T cell epitopes based on *M. tuberculosis* gene expression data (Zvi et al. 2008). RR-CDG and 5Ag were formulated in Addavax, a commercially available squalene-based oil-in-water nano-emulsion (Ott et al. 1995), to yield the experimental vaccine 5Ag/RR-CDG. Mice were vaccinated according to a standard vaccine schedule, receiving three immunizations of 5Ag/RR-CDG at 4 week intervals or one immunization with BCG 12 weeks prior to a low-dose aerosol challenge with the virulent Erdman strain of *M. tuberculosis*.

To determine whether 5Ag/RR-CDG elicits Th1 immunity, IFN-γ ELISPOT was performed using peripheral blood mononuclear cells (PBMCs) after each boost. 5Ag/RR-CDG generated T cell specific responses to Ag85B, ESAT-6, and Rv1733c that were dependent on RR-CDG and increased in magnitude after the second boost. Despite expressing four of the 5Ag antigens (not ESAT-6), BCG elicited significantly lower antigen specific T cell responses than 5Ag/RR-CDG Twelve weeks after the initial vaccination, mice were challenged with *M. tuberculosis*. At 4 weeks post challenge, 5Ag/RR-CDG vaccinated mice had 1 log fewer bacteria in the lungs when compared with PBS vaccinated mice, protection equivalent to that afforded by BCG. Importantly, this level of protection was durable out to 12 weeks post challenge, indicating that 5Ag/RR-CDG vaccinated mice may maintain elevated numbers of memory-derived CD4+ T cells (Carpenter et al. 2017).

To facilitate comparison to other vaccine adjuvants, RR-CDG was formulated with a fusion protein of ESAT-6 and Ag85B, antigens commonly used together in vaccine studies (Weinrich Olsen et al. 2001; Agger et al. 2008). At 12 weeks post infection, the protection afforded by RR-CDG and the ESAT-6/Ag85B fusion protein was equivalent to 5Ag/RR-CDG Thus, when combined with TB proteins, RR-CDG provides significant protective efficacy against *M. tuberculosis* challenge that is as effective as any other adjuvant tested in the context of a *M. tuberculosis* protein subunit vaccine to date (Aagaard et al. 2011; Skeiky et al. 2004; Bertholet et al. 2010; Baldwin et al. 2012; Billeskov et al. 2012; Ma et al. 2017).

5Ag/RR-CDG vaccine increases the percentage of parenchymal-homing T cells in the lungs relative to PBS or BCG vaccinated mice.

At the peak of the immune response, 4 weeks post challenge, mice vaccinated with 5Ag/RR-CDG had a significantly higher percentage of CD4+ T cells in the lungs compared to mice vaccinated with PBS and a corresponding decrease in the percentage of CD8+ T cells, suggesting that 5Ag/RR-CDG specifically promotes the recruitment and/or expansion of CD4+ T cells after infection. To examine antigen-specific T cell responses, cells from infected lungs were re-stimulated ex vivo with antigenic peptide pools. Due to the robust responses elicited by Ag85B and ESAT-6, only peptides from these antigens were used for post challenge intracellular cytokine staining (ICS) analyses. Ag85B-specific CD4+ IFN-γ+ T cell responses were only observed in 5Ag/RR-CDG immunized mice. A robust ESAT-6-specific CD4+ IFN-γ+ T cell population was observed in 5Ag/RR-CDG immunized mice, although it was lower than PBS immunized mice. A similar trend was observed for poly-functional T cells. In total, while 5Ag/RR-CDG vaccinated mice exhibited an increased frequency of total CD4+ T cells, there was not a strong correlation between protection and the presence of Ag85B- or ESAT-6-specific IFN-γ-producing CD4+ T cells in the lung.

Previous studies have identified two functional categories of CD4+ T cells during TB infection: CXCR3− KLRG1+ cells that localize to the lung vasculature and produce abundant levels of IFN-γ, and CXCR3+ KLRG1− cells that localize to the lung parenchyma and, despite producing lower levels of IFN-γ, are better at controlling $M.$ $tuberculosis$ infection (Sakai et al. 2014; Woodworth et al. 2017). At 4 weeks post challenge, there was no significant difference between the percentage of CXCR3− KLRG1+ vascular CD4+ T cells among the groups. However, there was a significant increase in the percentage of CXCR3+ KLRG1− parenchymal CD4+ T cells in the lungs of 5Ag/RR-CDG vaccinated mice compared to PBS controls. Although the percentage of CXCR3+ KLRG1− CD4+ T cells was higher in lungs of mice immunized with 5Ag/RR-CDG, a lower percentage of these cells produced IFN-γ when re-stimulated with Ag85B or ESAT-6 compared to PBS immunized mice. Thus, the 5Ag/RR-CDG vaccine elicits an increased frequency of CD4+ T cells and CXCR3+ KLRG1− T cell populations in the lungs, both of which are known to be protective against $M.$ $tuberculosis$.

To determine whether the antigen-specific T cell response and protective efficacy elicited by 5Ag/RR-CDG was dependent on STING and/or type I IFN signaling through the type I IFN receptor (IFNAR), mice lacking a functional copy of STING (Sting$^{gt/gt}$) (Sauer et al. 2011) or IFNAR (Ifnar$^{-/-}$) were immunized according to the schedule: BCG and prime CDN at wk −12; CDN boosts at wk −8, −4; ELISPOT/ICS at wk −7, −3; CFU/ICS at wk 4; and CFU at wk 12. Seven days after the 2$^{nd}$ boost, both Ag85B- and ESAT-6-specific T cell responses were undetectable in PBMCs from Sting$^{gt/gt}$ mice, indicating that antigen-specific T cell responses promoted by 5Ag/RR-CDG are STING-dependent. Interestingly, antigen-specific T cell responses were equivalent in wild-type and Ifnar$^{-/-}$ mice, suggesting that 5Ag/RR-CDG responses are not dependent on IFNAR signaling.

Sting$^{gt/gt}$ mice immunized with 5Ag/RR-CDG had equivalent CFU in the lungs at 4 and 12 weeks after challenge with $M.$ $tuberculosis$ compared to Sting$^{gt/gt}$ mice immunized with PBS, demonstrating that the protective efficacy of RR-CDG is dependent upon STING In contrast, Ifnar$^{-/-}$ mice immunized with 5Ag/RR-CDG had equivalent protection to wild-type 5Ag/RR-CDG vaccinated mice. Thus, while 5Ag/RR-CDG protection is STING-dependent, signaling through IFNAR is not necessary for the development of a protective immune response to $M.$ $tuberculosis$ challenge in 5Ag/RR-CDG vaccinated mice.

Example 2: Intranasal, but not Subcutaneous, Boosting of BCG with 5Ag/RR-CDG Significantly Enhances Protection from $M.$ $tuberculosis$ Challenge Following the vaccination schedule (CDN prime at wk −12; CDN boosts at wk −8, −4; ICS at wk −7; ELISPOT/ICS at wk −3; CFU/ICS at wk 4; and CFU at wk 12), BCG primed mice received two boosts of 5Ag/RR-CDG or 5Ag alone via SQ injection and were compared to mice that received three injections of 5Ag/RR-CDG as described above. After the 2$^{nd}$ boost, ELISPOT analysis showed that BCG immunized mice boosted SQ with 5Ag/RR-CDG had increased Ag85B- and ESAT-6-specific T cell responses compared to mice that were only immunized with BCG. However, there was no difference in IFN-γ levels between mice immunized with BCG and boosted with SQ 5Ag/RR-CDG compared to mice that received three SQ administrations of 5Ag/RR-CDG alone. Additionally, boosting BCG with SQ 5Ag/RR-CDG did not result in enhanced protection against $M.$ $tuberculosis$ aerosol challenge.

This was compared to mucosal administration of 5Ag/RR-CDG via the IN route to determine if intranasal boosting would enhance protection against $M.$ $tuberculosis$ infection using the BCG/CDN or CDN vaccination schedules (both supra) for IN boosting of BCG. As Addavax is not suitable for IN vaccination, 5Ag/RR-CDG was formulated in PBS. Seven days after the 2$^{nd}$ boost, IN administration of 5Ag/RR-CDG resulted in an increase in IFN-γ-producing Ag85B-specific CD4+ T cells in PBMCs compared to PBS vaccinated mice. However, significantly fewer IFN-γ producing cells were elicited by IN vaccination than by SQ vaccination. In contrast, IN administration of 5Ag/RR-CDG produced a robust IL-17 response from CD4+ T cells upon re-stimulation with Ag85B peptide pools, a response that was not observed with SQ administration of 5Ag/RR-CDG or with BCG vaccination.

Vaccinated mice were challenged with $M.$ $tuberculosis$ to determine the protective efficacy of IN delivered CDN vaccines. As expected, ~1 log of pulmonary protection was seen in mice vaccinated with either BCG or SQ 5Ag/RR-CDG However, IN administration of 5Ag/RR-CDG resulted in an additional ~0.5 log of control at 4 weeks post challenge and a trend towards increased control that was not statistically significant at 12 weeks. Remarkably, BCG vaccinated mice receiving IN boosts of 5Ag/RR-CDG had significantly lower CFU in the lungs at 12 weeks post challenge compared with BCG vaccination alone, resulting in greater than 2 logs of protection against infection. As with SQ vaccination, the percentage of CD4+ IFN-γ+ T cells in the lungs of IN vaccinated mice was not enhanced beyond infection-induced responses exhibited in PBS immunized mice at 4 weeks post challenge. However, the pre-challenge increase in Th17 cells noted in the blood was reflected post challenge with a large fraction of CD4+ T cells in the lungs producing IL-17. IN immunization or IN-based boosting of BCG with 5Ag/RR-CDG resulted in significantly more IL-17+ T cells than BCG vaccination or SQ administration of 5Ag/RR-CDG, both alone and as a booster vaccine. Thus, IN delivery of 5Ag/RR-CDG resulted in robust protection against infection, and had an additive effect when combined with BCG. Additionally, protection elicited via the IN route correlated not with increases in Th1 cells, but with increases in Th17 T cells.

Wild type mice and mice lacking IL-17 (Il17a−/−) were immunized with ML-RR-cGAMP formulated with 5Ag via the intranasal or subcutaneous route and subsequently challenged with Mtb. ML-RR-cGAMP resulted in equivalent protection to RR-CDG in wild type mice. The protection afforded by this vaccine was independent of IL-17 when delivered by the subcutaneous route. However, the additional protection afforded by intranasal administration was reduced in IL-17 deficient mice, demonstrating that IL-17 enhanced protection elicited via this route of vaccination.

Example 3: ML-RR-cGAMP, a Human STING Agonist, Elicits a Th17 Response and Protects Against Challenge with *M. tuberculosis*

RR-CDG efficiently activates murine STING; however, it does not engage all five common STING alleles in the human population (Corrales et al. 2015; Yi et al. 2013). The adjuvant activity of ML-RR-cGAMP, a dithio-substituted diastereomer of cGAMP with both a non-canonical 2'-5' and a canonical 3'-5' phosphodiester linkage (denoted mixed-linkage, ML) that is both resistant to hydrolysis by phosphodiesterases and a potent activator of these five common human STING alleles (Corrales et al. 2015) was tested for activity. Mice were immunized via the IN or SQ route with either 5Ag/RR-CDG or 5Ag/ML-RR-cGAMP, and the frequency of Ag85B-specific CD4+ T cells in the blood that produce either IL-17 or IFN-γ was measured 7 days after the $1^{st}$ boost. Both 5Ag/RR-CDG and 5Ag/ML-RR-cGAMP vaccines elicited IFN-γ-producing and IL-17-producing CD4+ T cells when administered IN. SQ administration of 5Ag/ML-RR-cGAMP did not elicit IL-17-producing T cells, but elicited more IFN-γ-producing T cells than IN immunization. This is similar to the trend seen with SQ vs. IN immunization of 5Ag/RR-CDG Mice vaccinated with 5Ag/ML-RR-cGAMP were challenged with virulent *M. tuberculosis* and protection was evaluated by CFU in the lungs at 4 weeks post challenge. Importantly, IN immunization with 5Ag/ML-RR-cGAMP provided ~1.5 logs of protection when used as a sole vaccine, equivalent to 5Ag/RR-CDG. These data demonstrate that ML-RR-cGAMP, a STING-activating compound with translational potential to human vaccines, behaves similarly to RR-CDG when used as an adjuvant in a protein subunit vaccine.

REFERENCES

Aagaard, C. et al., 2011. A multistage tuberculosis vaccine that confers efficient protection before and after exposure. *Nature medicine*, 17(2), pp. 189-194.

Agger, E. M., 2016. Novel adjuvant formulations for delivery of anti-tuberculosis vaccine candidates. *Advanced drug delivery reviews*, 102, pp. 73-82.

Agger, E. M. et al., 2008. Cationic liposomes formulated with synthetic mycobacterial cordfactor (CAF01): a versatile adjuvant for vaccines with different immunological requirements. M. M. Rodrigues, ed. *PLoS one*, 3(9), p.e3116.

Andersen, P. & Doherty, T. M., 2005. The success and failure of BCG—implications for a novel tuberculosis vaccine. *Nature Reviews Microbiology*, 3(8), pp. 656-662.

Baldwin, S. L. et al., 1998. Evaluation of new vaccines in the mouse and guinea pig model of tuberculosis. *Infection and Immunity*, 66(6), pp. 2951-2959.

Baldwin, S. L. et al., 2012. The importance of adjuvant formulation in the development of a tuberculosis vaccine. *The Journal of Immunology*, 188(5), pp. 2189-2197.

Bertholet, S. et al., 2010. A defined tuberculosis vaccine candidate boosts BCG and protects against multidrug-resistant *Mycobacterium tuberculosis*. *Science Translational Medicine*, 2(53), pp. 53ra74-53ra74.

Billeskov, R. et al., 2012. The HyVac4 subunit vaccine efficiently boosts BCG-primed anti-mycobacterial protective immunity. A. K. Tyagi, ed. *PloS one*, 7(6), p.e39909.

Blaauboer, S. M., Gabrielle, V. D. & Jin, L., 2014. MPYS/STING-mediated TNF-α, not type I IFN, is essential for the mucosal adjuvant activity of (3"-5")-cyclic-di-guanosine-monophosphate in vivo. *The Journal of Immunology*, 192(1), pp. 492-502.

Brandt, L. et al., 2000. ESAT-6 subunit vaccination against *Mycobacterium tuberculosis*. *Infection and Immunity*, 68(2), pp. 791-795.

Burdette, D. L. & Vance, R. E., 2012. STING and the innate immune response to nucleic acids in the cytosol. *Nature Immunology*, 14(1), pp. 19-26.

Burdette, D. L. et al., 2012. STING is a direct innate immune sensor of cyclic di-GMP. *Nature*, 478(7370), pp. 515-518.

Carpenter, S. M. et al., 2017. Vaccine-elicited memory CD4+ T cell expansion is impaired in the lungs during tuberculosis. P. Salgame, ed. *PLoS pathogens*, 13(11), p.e1006704.

Chandra, D. et al., 2014. STING ligand c-di-GMP improves cancer vaccination against metastatic breast cancer. *Cancer immunology research*, 2(9), pp. 901-910.

Chen, H. et al., 2011. Activation of STAT6 by STING is critical for antiviral innate immunity. *Cell*, 147(2), pp. 436-446.

Corrales, L. et al., 2015. Direct Activation of STING in the Tumor Microenvironment Leads to Potent and Systemic Tumor Regression and Immunity. *Cell reports*, 11(7), pp. 1018-1030.

Corrales, L. et al., 2016. The host STING pathway at the interface of cancer and immunity. *The Journal of clinical investigation*, 126(7), pp. 2404-2411.

Dey, B. et al., 2015. A bacterial cyclic dinucleotide activates the cytosolic surveillance pathway and mediates innate resistance to tuberculosis. *Nature medicine*, 21(4), pp. 401-406.

Dubensky, T. W., Kanne, D. B. & Leong, M. L., 2013. Rationale, progress and development of vaccines utilizing STING-activating cyclic dinucleotide adjuvants. *Therapeutic advances in vaccines*, 1(4), pp. 131-143.

Ebensen, T. et al., 2011. Bis-(3,5)-cyclic dimeric adenosine monophosphate: Strong Th1/Th2/Th17 promoting mucosal adjuvant. *Vaccine*, 29(32), pp. 5210-5220.

Ebensen, T., Schulze, K., Riese, P., Link, C., et al., 2007. The bacterial second messenger cyclic diGMP exhibits potent adjuvant properties. *Vaccine*, 25(8), pp. 1464-1469.

Ebensen, T., Schulze, K., Riese, P., Morr, M., et al., 2007. The bacterial second messenger cdiGMP exhibits promising activity as a mucosal adjuvant. *Clinical and vaccine immunology: CVI*, 14(8), pp. 952-958.

Fletcher, H. A. et al., 2016. T-cell activation is an immune correlate of risk in BCG vaccinated infants. *Nature Communications*, 7, pp. 11290-10.

Floyd, K., 2016. *Global Tuberculosis Report* 2016, World Health Organization. Available at: http://www.who.int/tb/publications/global_report/en/.

Flynn, J. L., 1993. An essential role for interferon gamma in resistance to *Mycobacterium tuberculosis* infection. *Journal of Experimental Medicine*, 178(6), pp. 2249-2254.

Gaffney, B. L. et al., 2010. One-flask syntheses of c-di-GMP and the [Rp,Rp] and [Rp,Sp] thiophosphate analogues. *Organic letters*, 12(14), pp. 3269-3271.

Gallegos, A. M. et al., 2011. A gamma interferon independent mechanism of CD4 T cell mediated control of *M.* tuberculosis infection in vivo. L. Ramakrishnan, ed. *PLoS pathogens,* 7(5), p.e1002052.

Gopal, R. et al., 2014. Unexpected role for IL-17 in protective immunity against hypervirulent *Mycobacterium tuberculosis* HN878 infection. D. M. Lewinsohn, ed. *PLoS pathogens,* 10(5), p.e1004099.

Green, A. M., Difazio, R. & Flynn, J. L., 2013. IFN-γ from CD4 T cells is essential for host survival and enhances CD8 T cell function during *Mycobacterium tuberculosis* infection. *Journal of immunology (Baltimore, Md.: 1950),* 190(1), pp. 270-277.

Hanson, M. C. et al., 2015. Nanoparticulate STING agonists are potent lymph node-targeted vaccine adjuvants. *The Journal of clinical investigation,* 125(6), pp. 2532-2546.

Horwitz, M. A. et al., 1995. Protective immunity against tuberculosis induced by vaccination with major extracellular proteins of *Mycobacterium tuberculosis*. *Proceedings of the National Academy of Sciences of the United States of America,* 92(5), pp. 1530-1534.

Hu, D.-L. et al., 2009. c-di-GMP as a vaccine adjuvant enhances protection against systemic methicillin-resistant *Staphylococcus aureus* (MRSA) infection. *Vaccine,* 27(35), pp. 4867-4873.

Ishikawa, H. & Barber, G. N., 2008. STING is an endoplasmic reticulum adaptor that facilitates innate immune signalling. *Nature,* 455(7213), pp. 674-678.

Iwasaki, A. & Medzhitov, R., 2010. Regulation of adaptive immunity by the innate immune system. *Science (New York, N.Y.),* 327(5963), pp. 291-295.

Kagina, B. M. N. et al., 2010. Specific T cell frequency and cytokine expression profile do not correlate with protection against tuberculosis after *bacillus* Calmette-Guérin vaccination of newborns. *American Journal of Respiratory and Critical Care Medicine,* 182(8), pp. 1073-1079.

Karaolis, D. K. R., Means, T. K., et al., 2007. Bacterial c-di-GMP is an immunostimulatory molecule. *The Journal of Immunology,* 178(4), pp. 2171-2181.

Karaolis, D. K. R., Newstead, M. W., et al., 2007. Cyclic di-GMP stimulates protective innate immunity in bacterial pneumonia. *Infection and Immunity,* 75(10), pp. 4942-4950.

Kaufmann, S. H. E., 2014. Tuberculosis vaccine development at a divide. *Current Opinion in Pulmonary Medicine,* 20(3), pp. 294-300.

Kaufmann, S. H. E., Weiner, J. & Reyn, von, C. F., 2017. Novel approaches to tuberculosis vaccine development. *International journal of infectious diseases: IJID: official publication of the International Society for Infectious Diseases,* 56, pp. 263-267.

Khader, S. A. et al., 2007. IL-23 and IL-17 in the establishment of protective pulmonary CD4+ T cell responses after vaccination and during *Mycobacterium tuberculosis* challenge. *Nature Immunology,* 8(4), pp. 369-377.

Khader, S. A. et al., 2005. IL-23 compensates for the absence of IL-12p70 and is essential for the IL-17 response during tuberculosis but is dispensable for protection and antigen-specific IFN-gamma responses if IL-12p70 is available. *The Journal of Immunology,* 175(2), pp. 788-795.

Langermans, J. A. M. et al., 2005. Protection of macaques against *Mycobacterium tuberculosis* infection by a subunit vaccine based on a fusion protein of antigen 85B and ESAT-6. *Vaccine,* 23(21), pp. 2740-2750.

Libanova, R. et al., 2010. The member of the cyclic di-nucleotide family bis-(3, 5)-cyclic dimeric inosine monophosphate exerts potent activity as mucosal adjuvant. *Vaccine,* 28(10), pp. 2249-2258.

Ma, J. et al., 2017. A Multistage Subunit Vaccine Effectively Protects Mice Against Primary Progressive Tuberculosis, Latency and Reactivation. *EBioMedicine,* 22, pp. 143-154.

Madhun, A. S. et al., 2011. Intranasal c-di-GMP-adjuvanted plant-derived H5 influenza vaccine induces multifunctional Th1 CD4+ cells and strong mucosal and systemic antibody responses in mice. *Vaccine,* 29(31), pp. 4973-4982. Available at: http://eutils.ncbi.nlm nih.gov/entrez/eutils/elink.fcgi?dbfrom=pubmed&id=21600260&retmode=ref&cmd=prlinks.

Marais, B. J. et al., 2016. Interrupted BCG vaccination is a major threat to global child health. *The Lancet. Respiratory medicine,* 4(4), pp. 251-253.

McWhirter, S. M. et al., 2009. A host type I interferon response is induced by cytosolic sensing of the bacterial second messenger cyclic-di-GMP. *Journal of Experimental Medicine,* 206(9), pp. 1899-1911.

Ogunniyi, A. D. et al., 2008. c-di-GMP is an effective immunomodulator and vaccine adjuvant against pneumococcal infection. *Vaccine,* 26(36), pp. 4676-4685.

Olsen, A. W. et al., 2004. Protective effect of a tuberculosis subunit vaccine based on a fusion of antigen 85B and ESAT-6 in the aerosol guinea pig model. *Infection and Immunity,* 72(10), pp. 6148-6150.

Ott, G et al., 1995. MF59. Design and evaluation of a safe and potent adjuvant for human vaccines. *Pharmaceutical biotechnology,* 6, pp. 277-296.

Rappuoli, R. et al., 2011. Vaccines for the twenty-first century society. *Nature reviews. Immunology,* 11(12), pp. 865-872.

Sakai, S. et al., 2014. Cutting Edge: Control of *Mycobacterium tuberculosis* Infection by a Subset of Lung Parenchyma-Homing CD4 T Cells. *The Journal of Immunology,* 192(7), pp. 2965-2969.

Sauer, J.-D. et al., 2011. The N-ethyl-N-nitrosourea-induced Goldenticket mouse mutant reveals an essential function of Sting in the in vivo interferon response to *Listeria monocytogenes* and cyclic dinucleotides. *Infection and Immunity,* 79(2), pp. 688-694.

Skeiky, Y. A. W. et al., 2004. Differential immune responses and protective efficacy induced by components of a tuberculosis polyprotein vaccine, Mtb72F, delivered as naked DNA or recombinant protein. *The Journal of Immunology,* 172(12), pp. 7618-7628.

Skjøt, R. L. et al., 2000. Comparative evaluation of low-molecular-mass proteins from *Mycobacterium tuberculosis* identifies members of the ESAT-6 family as immunodominant T-cell antigens. *Infection and Immunity,* 68(1), pp. 214-220.

Tamayo, R., Pratt, J. T. & Camilli, A., 2007. Roles of cyclic diguanylate in the regulation of bacterial pathogenesis. *Annual review of microbiology,* 61(1), pp. 131-148.

Tameris, D. M. D. T. et al., 2013. Safety and efficacy of MVA85A, a new tuberculosis vaccine, in infants previously vaccinated with BCG: a randomised, placebo-controlled phase 2b trial. *The Lancet,* 381(9871), pp. 1021-1028.

Wassermann, R. et al., 2015. *Mycobacterium tuberculosis* Differentially Activates cGAS- and Inflammasome-Dependent Intracellular Immune Responses through ESX-1. *Cell Host and Microbe,* 17(6), pp. 1-13.

Watson, R. O. et al., 2015. The Cytosolic Sensor cGAS Detects *Mycobacterium tuberculosis* DNA to Induce Type I Interferons and Activate Autophagy. *Cell Host and Microbe,* 17(6), pp. 1-10.

Weinrich Olsen, A. et al., 2001. Protection of mice with a tuberculosis subunit vaccine based on a fusion protein of antigen 85b and esat-6. *Infection and Immunity*, 69(5), pp. 2773-2778.

Woo, S.-R. et al., 2014. STING-dependent cytosolic DNA sensing mediates innate immune recognition of immunogenic tumors. *Immunity*, 41(5), pp. 830-842.

Woodworth, J. S. et al., 2017. Subunit vaccine H56/CAF01 induces a population of circulating CD4 T cells that traffic into the *Mycobacterium tuberculosis*-infected lung. *Mucosal Immunology*, 10(2), pp. 555-564.

Yan, H. et al., 2009. 3",5-" Cyclic diguanylic acid elicits mucosal immunity against bacterial infection. *Biochemical and biophysical research communications*, 387(3), pp. 581-584.

Yi, G et al., 2013. Single nucleotide polymorphisms of human STING can affect innate immune response to cyclic dinucleotides. K. Li, ed. *PloS one*, 8(10), p.e77846.

Young, D. & Dye, C., 2006. The development and impact of tuberculosis vaccines. *Cell*, 124(4), pp. 683-687.

Zvi, A. et al., 2008. Whole genome identification of *Mycobacterium tuberculosis* vaccine candidates by comprehensive data mining and bioinformatic analyses. *BMC medical genomics*, 1(1), p. 18.

The invention claimed is:

1. A method of prophylactic or therapeutic vaccination of a human against *Mycobacterium tuberculosis* (*M. tuberculosis*) comprising:
   intranasally administering a first vaccine component comprising one or more *M. tuberculosis*, *Mycobacterium vaccae* (*M. vaccae*) or *Mycobacteroium bovis* (*M. bovis*) antigens,
   intranasally administering a second vaccine component comprising a Stimulator of Interferon Genes (STING) activator, wherein the STING activator is a cyclic dinucleotide (CDN).

2. The method of claim 1, wherein the first vaccine component comprises *Bacillus* Calmette-Guérin (BCG).

3. The method of claim 1, wherein the first vaccine component comprises one or more recombinantly expressed proteins that comprise antigens from *M. tuberculosis*.

4. The method of claim 1, wherein the first vaccine component comprises an antigen selected from the group consisting of *Mycobacterium tuberculosis* antigen 85A (Ag85A), *Mycobacterium tuberculosis* antigen 85B (Ag85B), *Mycobacterium tuberculosis* secreted protein ESAT6 (ESAT6), *Mycobacterium tuberculosis* resuscitation-promoting factor D (RpfD), *Mycobacterium tuberculosis* RpfB, culture filtrate protein (CFP-10), *Mycobacterium tuberculosis* secreted protein MPT-64 (MPT-64), *Mycobacterium tuberculosis* phosphate transporter subunit PstS1 (Pst-S1), *Mycobacterium tuberculosis* alanine and proline-rich secreted protein (Apa), *Mycobacterium tuberculosis* chaperone protein GroES (GroES), *Mycobacterium tuberculosis* chaperone protein GroEL (GroEL), *Mycobacterium tuberculosis* chaperone protein DnaK (DnaK), *Mycobacterium tuberculosis* ESX-1 secretion-associated protein EspC (EspC), *Mycobacterium tuberculosis* phosphate-specific transport system accessory protein PhoU (PhoY2), *Mycobacterium tuberculosis* protein 8.4 (Mtb8.4), *Mycobacterium tuberculosis* protein 10.4 (Mtb10.4), *Mycobacterium* heat shock protein X (HspX), *Mycobacterium tuberculosis* protein Rv1733c (Rv1733c), *Mycobacterium tuberculosis* protein Rv2626c (Rv2626c), *Mycobacterium tuberculosis* protein Rv1886 (Rv1886), *Mycobacterium tuberculosis* protein Rv2875 (Rv2875), *Mycobacterium tuberculosis* protein Rv3407 (Rv3407), and *Mycobacterium tuberculosis* protein Rv3478 (Rv3478).

5. The method of claim 1, wherein the first vaccine component comprises a plurality of antigens selected from the group consisting of Ag85A, Ag85B, ESAT6, RpfD, RpfB, CFP-10, MPT-64, Pst-S1, Apa, GroES, GroEL, DnaK, EspC, PhoY2, Mtb8.4, Mtb10.4, HspX, Rv1733c, Rv2626c, Rv1886, Rv2875, Rv3407, and Rv3478.

6. The method of claim 1, wherein the first vaccine component comprises a 2Ag fusion of Ag85B and ESAT-6, a 3Ag fusion of Ag85B, ESAT-6 and CFP-10, or a 5Ag fustion of Ag85B, ESAT-6, Rv1733c, Rv2626c, and Rv2389c (RpfD).

7. The method of claim 1, wherein the STING activator is a cyclic dinucleotide (CDN), and the CDN is a cyclic diguanosine (CDG) or a cyclic guanosine monophosphate-adenosine monophosphate (cGAMP).

8. The method of claim 1, wherein the STING activator is a cyclic dinucleotide (CDN), and the CDN is a phosphodiesterase-resistant synthetic form.

9. The method of claim 1, wherein the STING activator is a cyclic dinucleotide (CDN), and the CDN is RR-CDG or mixed link (ML)-RR-cGAMP, wherein RR refers to R,R stereochemical configuration, wherein R is short for Latin rectus for right.

10. The method of claim 1, wherein:

the first vaccine component comprises a 2Ag fusion of Ag85B and ESAT-6, a 3Ag fusion of Ag85B, ESAT-6 and CFP-10, or, preferably, a 5Ag fusion of Ag85B, ESAT-6, Rv1733c, Rv2626c, and Rv2389c (RpfD); and the STING activator is a cyclic dinucleotide (CDN), and the CDN is RR-CDG or ML-RR-cGAMP.

11. The method of claim 1, wherein the first vaccine component and the second vaccine component are administered as a single composition.

12. The method of claim 1, wherein the composition is administered in an aqueous vehicle.

13. The method of claim 1, wherein the vaccine composition for intranasal administration comprises a third vaccine component that is an adjuvant.

14. The method of claim 13, wherein the adjuvant is selected from the group consisting of water in oil emulsion, dimethyl dioctadecyl ammoniumbromide, monophosphoryl lipid A-trehalose dicorynomycolate adjuvant, Quillaia saponaria saponins, squalene oil-in-water emulsion adjuvant monophosphoryl lipid A adjuvant, two component antibacterial peptide-synthetic oligodeoxynucleotide adjuvant, *Escherichia coli* heat labile enterotoxin adjuvant, two-component α,α'-trehalose 6,6'-dibeheneate-N,N'-dimethyl-N,N'-dioctadecylammonium adjuvant, CpG oligos, diethylethanolamine-dextran, and aluminum hydroxide.

15. The method of claim 1, wherein the first vaccine component is administered as a priming vaccine and the second vaccine component is administered as a boost component in a prime-boost vaccination protocol.

16. The method of claim 1, wherein the first vaccine component and the second vaccine component are administered as a priming vaccine in a prime-boost vaccination protocol.

17. The method of claim 1, wherein the first vaccine component and the second vaccine component are administered as a boost component in a prime-boost vaccination protocol.

18. A vaccine formulated for intranasal administration, comprising:
  a first vaccine component comprising one or more *Mycobacterium tuberculosis*, *Mycobacterium* vaccae or *Mycobacteroium bovis* antigens, and
  a second vaccine component comprising a Stimulator of Interferon Genes (STING) activator, wherein the STING activator is a cyclic dinucleotide (CDN),
  wherein the first vaccine component and the second vaccine component are combined in an aqueous vehicle.

* * * * *